United States Patent [19]
Hsia et al.

[11] Patent Number: 6,059,772
[45] Date of Patent: *May 9, 2000

[54] APPARATUS AND METHOD FOR TREATING GLAUCOMA USING A GONIOSCOPIC LASER TRABECULAR ABLATION PROCEDURE

[75] Inventors: James C. Hsia, Andover, Mass.; Shlomo Melamed, Raanana, Israel; Joseph A. Lowery, Charlestown, Mass.

[73] Assignee: Candela Corporation, Wayland, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/781,504

[22] Filed: Jan. 8, 1997

Related U.S. Application Data

[63] Continuation of application No. 08/402,005, Mar. 10, 1995, abandoned.

[51] Int. Cl.$^7$ ...................................................... A61N 5/06
[52] U.S. Cl. ........................ 606/4; 606/2; 606/3; 606/11; 606/13
[58] Field of Search ....................................... 606/2, 3–14

[56] References Cited

U.S. PATENT DOCUMENTS

| | | | |
|---|---|---|---|
| 3,828,788 | 8/1974 | Krasnov et al. | 138/303.1 |
| 4,791,927 | 12/1988 | Menger | 606/3 |
| 5,549,596 | 8/1996 | Latina . | |

FOREIGN PATENT DOCUMENTS

90/11054  10/1990  WIPO ..................................... 606/10

OTHER PUBLICATIONS

Moulin et al.; Trabeculoperforation? Trabeculoretraction? Trabeculoplasty?; Ophthalomologica, Basel 191:73–83 (1985).

Hill et al.; Laser Trabecular Ablation (LTA); Lasers in Surgery and Medicine 11:341–346 (1991).

Goldschmidt et al.; Theoretical Approach to Laser Trabeculotomy; Med. Phys. 5(2) 92–99 (1978).

Melamed: Nd: YAG Laser Trabeculopuncture: Obstacles and Hopes on the Way to Glaucoma Treatment; Opth. Laser Therapy 2(4) 227–237 (1987).

M. Krasnov; Laseropuncture of Anterior Chamber Angle in Glaucoma; Am. J. Ophthalmology 75(4) 674–678 (1973).

Del Priore et al.; Long–Term Follow–Up of Neodymium: YAG Laser Angle Surgery for Open–Angle Glaucoma; Ophthalmology 95(2) 277–281 (1988).

Robin et al.; Q–Switched Neodymium–YAG Laser Angle Surgery in Open–Angle Glaucoma; Arch. Ophthalmol 103: 793–795 (1985).

M. Krasnov; Q–Switched Laser Iridectomy and Q–Switched Laser Goniopuncture; Adv. Ophthal. 34: 192–196 (1977).

B. Witschel et al.; Experimental Studies on Laser Trabeculo–Puncture; Adv. Ophthal. 34:197–200 (1977).

F. Fankhauser et al.; Thermal Effects on the Trabecular Meshwork Induced by Laser Irradiation: Clinical Implications Deduced from Ultrastructural Studies on the Macaca Speciosa Monkey; Trans. Opht. Soc. U.K. 105:555–561 (1986).

(List continued on next page.)

*Primary Examiner*—David M. Shay
*Attorney, Agent, or Firm*—Testa, Hurwitz & Thibeault, LLP

[57] ABSTRACT

A non-invasive apparatus and method for treating open angle glaucoma in a human eye comprises thermally ablating a targeted region of the trabecular meshwork of a human eye by irradiating the region with a beam of pulsed laser radiation. The beam of pulsed radiation has a wavelength between 350 and 1300 nanometers, energy of 10 to 500 millijoules per pulse, and pulse duration of 0.1 to 50 microseconds. The beam is non-invasively delivered gonioscopically through the cornea onto a targeted region of the trabecular meshwork. The targeted region of the trabecular meshwork is illuminated at a spot size of between 50 and 300 microns in diameter.

10 Claims, 2 Drawing Sheets

OTHER PUBLICATIONS van der Zypen et al.; The Ultrastructure Features of Laser Trabeculopuncture and Cyclodialysis; Ophth. 179:189–200 (1979).

S. Venkatesh et al.; In Vitro Studies with a Pulsed Neodymium/YAG Laser; British J. of Ophth. 69:86–91 (1985).

Kitazawa et al.; Q–Switched Nd: YAG Laser for Developmental Glaucoma; Ophthalmic Surgery 13(2): 99–100 (1985).

Melamed et al.; Nd: YAG Laser Trabeculopuncture in Angle–Recession Glaucoma; Opth. Surgery 23(1): 31–35 (1992).

Melamed et al.; Neodymium: YAG Laser Trabeculopuncture in Juvenile Open–Angle Glaucome; Opth. 94(2):163–170 (1987).

Vogel et al.; Die Ablation des Trabekelwerks; Klin. Mbl. Augenheilk 197:250–253 (1990).

Meyer et al.; Corneal Endothelial Damage with Neodymium: YAG Laser; Ophthalmology 91(9): 1022–1028 (1984).

Gaasterland et al.; Long–Term Effects of Q–Switched Ruby Laser on Monkey Anterior Chamber Angle; Invest. Ophth. & Vis. Sci. 26(2):129–135 (1985).

Wickham et al.; Physiological Effects of Laser Trabeculotomy in Rhesus Monkey Eyes; Invest. Ophtalmol. Visual Sci. 16(7):624–628 (1977).

Lowery/Simon Abstract; Gonioscopic Laser Trabecular Ablation . . . and Scanning Electron Microscopy (1994).

Senft et al.; Neodymium–YAG Laser Goniotomy vs Surgical Goniotomy; Arch. Optthalmol 107:1773–1776 (1989).

APPARATUS AND METHOD FOR TREATING GLAUCOMA USING A GONIOSCOPIC LASER TRABECULAR ABLATION PROCEDURE

This is a continuation of copending application Ser. No. 08/402,005 filed on Mar. 10, 1995.

BACKGROUND

The invention relates generally to method and laser apparatus for treating glaucoma in a human eye. In particular, the invention relates to a method and laser apparatus for treating open angle glaucoma using a gonioscopic laser trabecular ablation procedure.

Open angle glaucoma is a potentially debilitating disease of the eye which, if left untreated, may lead to blindness. While the cause for open angle glaucoma is not well understood, all existing treatments are aimed at lowering intraocular pressure to slow or arrest the progression of the disease. Intraocular pressure reduction can be achieved using drugs. However, drugs are often not effective or their effect diminishes over time. When this happens, various surgical procedures are performed to lower intraocular pressure.

These surgical procedures are generally aimed at either decreasing the production of the aqueous humor or increasing the outflow facility in the eye. Examples of the former includes cyclo-destructive procedures which are aimed at killing a percentage of the ciliary processes that produce aqueous humor in the eye. Examples of the latter include procedures such as trabeculectomy and laser trabeculoplasty.

With respect to the latter procedures, it has been shown that the site of the greatest outflow resistance is at the trabecular meshwork. The trabecular meshwork is a fibrous structure situated at the edge of the cornea in the region of the anterior chamber known as the angle. The aqueous humor drains through the trabecular meshwork into Schlemm's canal. Investigators have experimented with various surgical procedures aimed at creating holes in the meshwork, extending into Schlemm's canal, postulating that outflow facility would be improved.

For example, in the 1970's, an investigator used a Q-switched ruby laser to create holes in the trabecular meshwork. The pulses of laser energy were delivered using a goniolens, and the pulse duration was on the order of 30 nanoseconds. For this procedure, the mechanism for hole creation is optical breakdown, which occurs at the focus of high peak power laser beams. The optical breakdown creates a mechanical shockwave which then mechanically tears a hole in the meshwork. This procedure did achieve significant intraocular pressure reduction in a large percentage of the subjects. However, a problem with the procedure was that the pressure-lowering effect lasted only about three months on average.

Other investigators studied a similar procedure using Q-switched Nd:YAG lasers with pulse durations in the 10 nanosecond range. Similar results to the ruby laser described above were achieved for primary open angle glaucoma. However, only a subgroup of subjects suffering from juvenile glaucoma benefited over the long term from this treatment.

More recently, another group of investigators proposed using mid-infrared (i.e., a near 3 micron wavelength) laser radiation to ablate holes in the meshwork. The goal of this procedure is to create holes extending directly into Schlemm's canal. However, because the 3 micron energy is strongly absorbed by water which is prevalent in the eye, the laser energy must be delivered by a fiber that is physically brought into contact with the trabecular meshwork. In other words, the procedure is invasive. It is speculated that because of the strong water absorption of the laser radiation, a clean ablation hole can be created in the meshwork with minimal collateral thermal damage. A significant disadvantage of the proposed procedure is the invasive nature of the treatment.

Laser trabeculoplasty is another accepted procedure for the treatment of open angle glaucoma. This procedure is commonly performed using either a cw argon laser or a cw diode laser. In this procedure, the laser energy is delivered gonioscopically using a contact goniolens. The laser energy is focused into a 50–100 micron diameter spot on the trabecular meshwork. The laser energy heats the meshwork tissue until a white spot (or laser burn) is created. Over 100 such spots may be created over the entire 360° area of the meshwork. Interestingly, no meshwork tissue is actually ablated or removed, and no holes are created in the meshwork. This procedure has been effective in lowering intraocular pressure in over 80% of the subjects.

Although the exact mechanism which causes the reduction of intraocular pressure in laser trabeculoplasty has never been fully elucidated, it is generally accepted that the laser burns cause shrinkage in the trabecular meshwork tissue. This shrinkage is believed to cause the meshwork tissue disposed between the laser burns to stretch and become more open, thereby decreasing the resistance of the trabecular meshwork to aqueous outflow.

A problem with laser trabeculoplasty is that the intraocular pressure lowering effect tends to disappear over time. In approximately 50% of the subjects treated with this procedure, intraocular pressure can be adequately controlled for less than about four to five years. For subjects subjected to laser trabeculoplasty and having an intraocular pressure that can no longer be adequately controlled, repeated laser trabeculoplasty is of limited value. In such cases, the only viable alternative is filtration surgery.

Another problem commonly encountered with laser trabeculoplasty is the phenomenon of pressure spiking, where in the days immediately following the trabeculoplasty procedure, the subject's intraocular pressure rises above pretreatment levels. This spiking requires careful monitoring and control with drugs.

It is therefore a principle object of the present invention to provide a non-invasive method and laser apparatus for treating open angle glaucoma using a gonioscopic laser trabecular ablation procedure which results in long term intraocular pressure control.

It is another principle object of the present invention to provide a non-invasivemethod and apparatus for treating open angle glaucoma for subjects who utimately failed laser trabeculoplasty treatment.

SUMMARY OF THE INVENTION

The present invention features a totally non-invasive gonioscopic laser trabecular ablation procedure for treating glaucoma in the human eye. The invention utilizes a beam of pulsed laser radiation having a set of parameters specifically selected to (i) thermally ablate a targeted region of the trabecular meshwork, (ii) minimize the occurrence of mechanical shockwave effects, and (iii) minimize thermal necrosis of surrounding tissues. For example, the wavelength (or color) of the laser beam is chosen to maximize absorption in the targeted region of the trabecular meshwork and minimize absorption and scattering by the cornea and aqueous humor. The pulse duration of the laser beam is selected based on the thermal relaxation time of the target. That is, the pulse duration is shorter than the thermal relaxation so that only the targeted material is heated and the surrounding tissue is unaffected.

In one embodiment, the invention features a non-invasive method of treating open angle glaucoma in a human eye comprising thermally ablating a targeted region of the trabecular meshwork of a human eye by irradiating that region with a beam of pulsed laser radiation. The beam of pulsed radiation has a wavelength between 350 and 1300 nanometers, energy of 10 to 500 millijoules per pulse, and pulse duration of 0.1 to 50 microseconds. The beam is non-invasively delivered gonioscopically (i.e., by a goniolens) through the cornea onto a targeted region of the trabecular meshwork. The targeted region of the meshwork is illuminated at a spot size of between 50 and 300 microns in diameter.

The beam of pulsed laser radiation may be generated by a Ti:Sapphire laser and delivered to the eye by a slit lamp delivery system. Further, the beam of pulsed radiation may have a wavelength of between 700 and 900 nanometers, a pulse duration of one to 50 microseconds, energy of 25 to 250 millijoules and a spot size of 100 to 200 microns in diameter.

In another embodiment, the invention features an apparatus for non-invasive treatment of open angle glaucoma in a human eye. The apparatus includes a laser and a slit lamp delivery system. The laser, which may be a Ti:Sapphire laser, is configured to generate a beam of pulsed laser radiation of wavelength between 700 and 900 nanometers, energy of 10 to 500 millijoules per pulse, and pulse duration of 0.1 to 50 microseconds. The delivery system is configured to deliver the beam of pulsed laser radiation gonioscopically to a region of the trabecular meshwork of a human eye. The delivery system includes a goniolens which directs the laser beam through the cornea onto a targeted region of the trabecular meshwork.

A series of experiments has shown that human subjects treated using the non-invasive method of the invention exhibit long term reduction in intraocular pressure. An explanation for the pressure reduction effect of the present method is that the laser beam has been optimized to thermally ablate material disposed, thereby increasing the outflow facility. It is believed that the present method is less likely to elicit a healing response such that long term pressure reduction can be achieved.

BRIEF DESCRIPTION OF THE DRAWINGS

These and other features of the invention are more fully described below in the detailed description and accompanying drawings of which the figures illustrate a method and laser apparatus for non-invasive glaucoma.

DETAILED DESCRIPTION OF THE INVENTION

The present invention contemplates a system and non-invasive method for treating glaucoma which includes delivering a beam of pulsed laser radiation to thermally ablate regions of the trabecular meshwork of a human eye. In accordance with the invention, the laser beam has a set of pulse parameter ranges carefully selected to (i) thermally ablate targeted tissue of the trabecular meshwork, (ii) minimize the occurrence of mechanical shockwave effects, and (iii) minimize thermal necrosis of surrounding tissue. As a result, subjects treated using the non-invasive method of the invention exhibit long term reduction in intraocular pressure.

Figure 1:
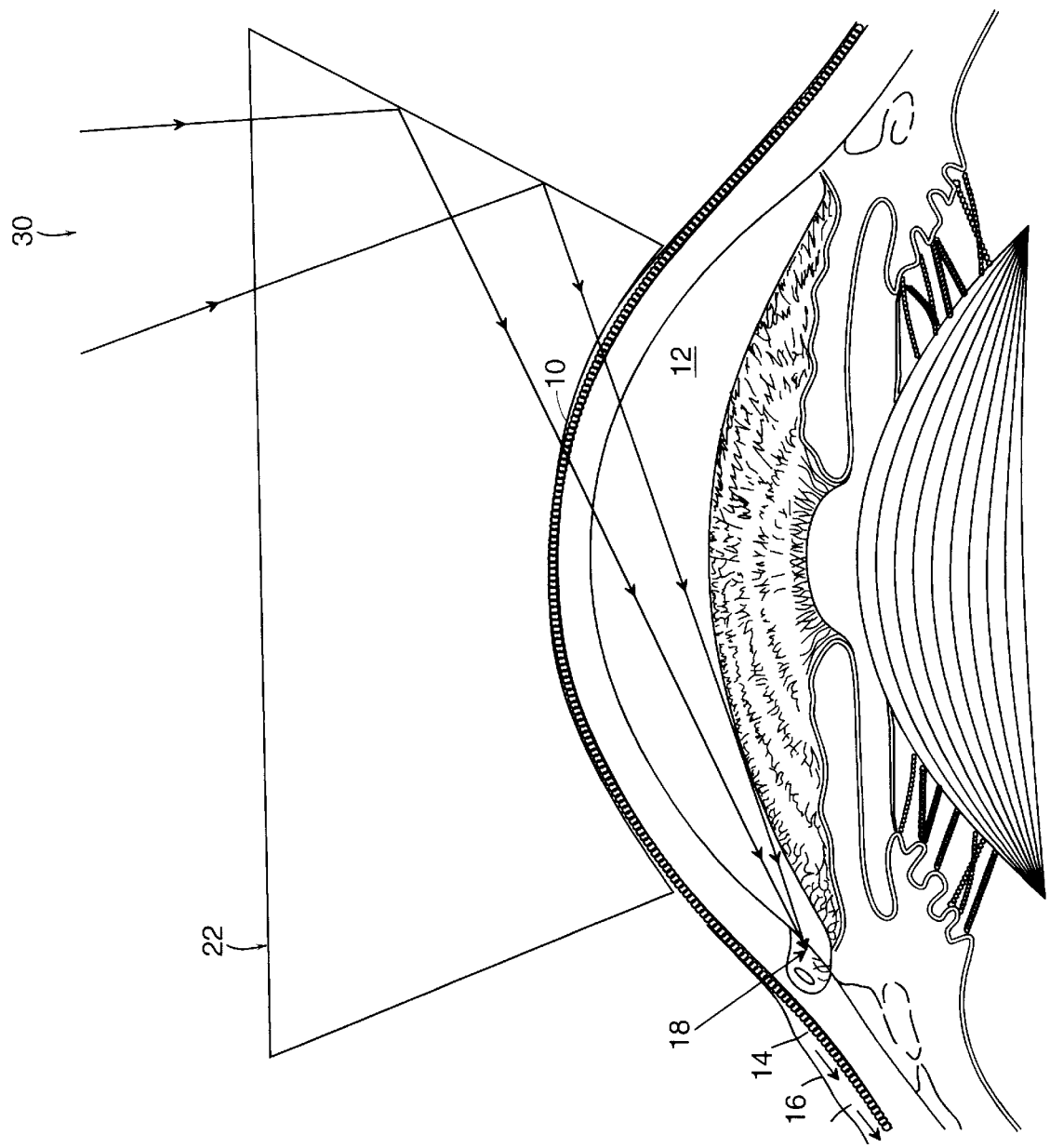
FIG. 1 is a cross-sectional view of a human eye beig subjected to gonioscopic trabecular laser ablation procedure in accordance with the invention.

FIG. 1 depicts a cross-sectional view of a human eye treated using the gonioscopic trabecular laser ablation procedure of the invention. The cornea 10 is a protruding anterior transparent portion of the eye. Situated behind the cornea is the anterior chamber 12. The eye also includes a sclera 14, which is a tough white outer envelope of tissue that covers all of the exterior of the eyeball other than the cornea. The sclera is covered by a conjunctiva 16 at the anterior section. The trabecular meshwork 18 is a reticular (or fibrous) structure situated at the edge of the cornea adjacent the outer angle of the anterior chamber. The trabecular meshwork includes a plurality of fibers, wherein the intervals between the fibers form small spaces. These spaces provide a fluid communication path with the canal of Schlemn (not shown). The beam 46 of pulsed radiation is generated by a Ti:Sapphire laser 42 and delivered into the eye by a slit lamp delivery system, including a goniolens 22 (see FIG. 2).

The beam has a set of pulse parameter ranges specifically selected to thermally ablate targeted tissue of the trabecular meshwork, while minimizing damage to surrounding tissue. In particular, the wavelength of the laser beam has been chosen to maximize absorption in the targeted region of the trabecular meshwork and minimize absorption and scattering by the cornea and aqueous humor. Thus, the beam has a wavelength between 350 and 1300 nanometers, or between 700 and 900 nanometers in one detailed embodiment. Within this wavelength range, trabecular meshwork absorption, as well as scattering by liberated particulate and blood absorption, are stronger at shorter wavelengths. Since the beam may liberate particulate and perhaps some small amount of blood into the aqueous, shorter wavelength radiation may be prevented from effectively irradiating the meshwork after a few laser pulses. The exact wavelength used for a particular subject depends on trade-offs between strong absorption by the meshwork and transmission by the aqueous humor.

The pulse duration of the laser beam is chosen to have a high probability of thermally ablating material of the trabecular meshwork, but to have a minimal shockwave effect so that the tissue does not tear when irradiated. Moreover, the pulse duration is selected to be shorter than the thermal relaxation of the target so that only the targeted material is heated and the surrounding tissue is unaffected. Thus, the pulse duration is between 0.1 and 50 microseconds, or between 1 and 50 microseconds in one detailed embodiment.

It is known that the trabecular meshwork includes melanin in certain groups of people. As such, if the present method thermally ablates melanin particles in the trabecular meshwork, then the thermal relaxation is in the range of microseconds for micron-sized particles. Moreover, to avoid the generation of strong shockwaves that tend to tear the meshwork, microsecond range pulses are desired, consistent with effective heating of the targeted meshwork tissue.

The pulse energy is chosen to facilitate thermal ablation and minimize the shockwave effect of the laser light.

Generally, the pulse energy is between 10 and 500 millijoules. Energy between 10 and 250 millijoules allows for use of a relatively low energy level with multiple laser pulses such as 10 to 50 pulses. For use of only a few pulses, a higher energy of between 100 and 500 millijoules per pulse may be used.

The spot diameter is chosen such that sufficient laser energy density is provided to facilitate thermal ablation of the trabecular meshwork tissue. The spot size the present method is 50 to 300 microns. In one detailed embodiment, the spot size is on the order of the width of the meshwork, i.e. in the range of 100 to 200 microns.

Figure 2:
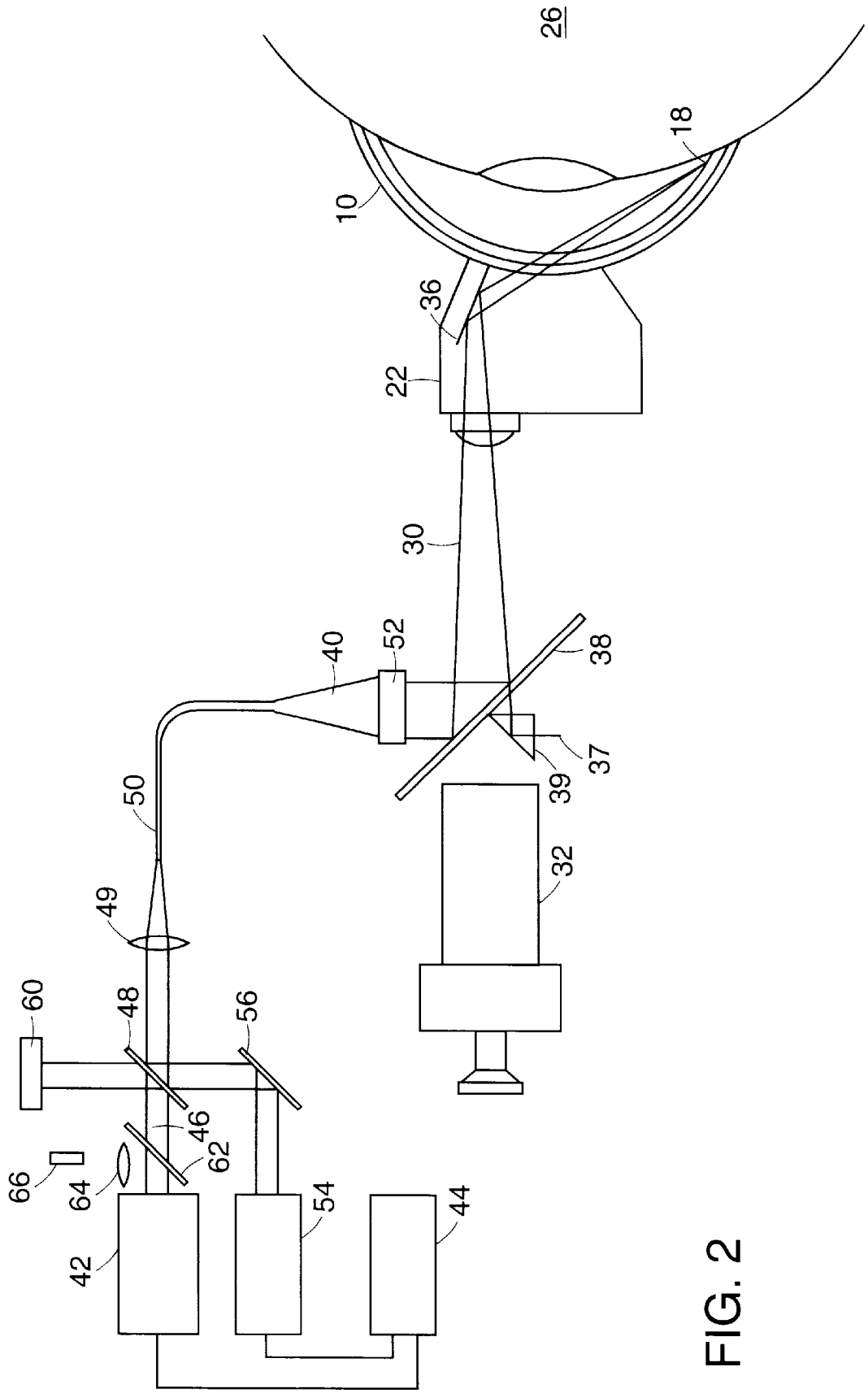
FIG. 2 is a schematic illustration of a laser system for treating open angle glaucoma in accordance with the gonioscopic trabecular laser ablation procedure of the invention.

FIG. 2 illustrates a laser system for treating open angle glaucoma in accordance with the gonioscopic trabecular laser ablation procedure of the invention. In the case of glaucoma disease, there is excessive pressure in the ocular fluid in the region 26 which can lead to loss of visual acuity if not treated.

A slit lamp delivery system 24 is utilized for applying the beam 20 of laser radiation provided by a laser 42 to the region 26. In particular, the slit lamp delivery system includes an optical path 30 and a microscope system 32. An operator views the region along the path 30 through a goniolens 22, which has a side reflector 36. A slit beam may be projected along an axis 37 and reflected by a prism 39 to be focused on the region 24.

The goniolens is adapted to withstand the high peak powers of the laser and possesses a mirror angle appropriate for use in the method of this invention. The lens is an aberration-free, entirely glass lens. One surface has a 68° angle and is configured to provide a reflecting surface.

The optical path 30 includes a dichroic turning mirror 38 which permits radiation from an optical path 40 to be introduced onto the path 30. Alternatively, the dichroic mirror may be replaced with a small turning mirror around which the operator may view along the optical path 30. Radiation applied to the optical path 40 includes radiation from a Ti:Sapphire laser 42 controlled by an operator to generate pulses by a control system 44. An output beam 46 from the laser 42 is applied past a shutter mechanism 48 through a lens system onto a quartz optic fiber 50. The fiber conducts the radiation from the laser assembly, typically located at some distance, to the laser beam path 40. The diverging radiation from the fiber 50 is collimated and focused by a lens system 52. The light is reflected by the mirror 38 through the goniolens 22 and, when reflected by the reflector 36, comes to a focus at a targeted region of the trabecular meshwork 18 of the eye.

The slit lamp delivery system may further include an aiming laser such as a relatively low power helium-neon laser 54. The output beam from the aiming laser is reflected by a mirror 56 and shutter mirror 48 into the optic fiber 50 to occupy the same path 40 as the beam 46 from the laser 42. In this manner, the aiming laser 54 can provide a non-damaging light beam following the same path and focused to the same point as the radiation from the beam 46. The operator, through manipulation of the slit lamp delivery system, positioning of the eye, and, particularly, with fine adjustment by manual positioning of the goniolens 22, adjusts the point of aim of the low power laser beam from laser 54 to the region of the trabecular meshwork where it is desired to provide laser ablation.

While the shutter mechanism 48 is positioned to reflect the aiming beam toward the optic fiber 50, the laser may be fired and the beam from the laser is then reflected from the back side of the shutter 48 to a light absorbing medium 60. Within the path between the laser 42 and the shutter 48 there is positioned a beam splitter 62 which reflects about five percent of the laser beam through a lens 64 to a pyroelectric detector 66 which serves as an energy monitor. With this system, the laser can be fired as necessary to obtain the correct energy level before exposing the eye to the laser.

Once the aim point has been established and the proper energy level has been established, the shutter 48 is switched and the operator, through control 44, activates the laser 42 for pulse application of radiation. The laser 42 has produces laser radiation that is absorbed preferentially by the trabecular meshwork. The high power beam from the laser 42 following along the aim path established by the low power beam from the aim laser 54, causes thermal ablation of targeted material of the trabecular meshwork.

A series of experiments has shown that human subjects treated using the non-invasive method and laser apparatus of the invention exhibit long term reduction in intraocular pressure. In one experiment, two subjects were subjected to the laser trabecular ablation procedure. Each subject was exposed to a series of laser pulses having a wavelength on the order of 800 nanometers and pulse durations on the order of microseconds.

One subject's intraocular pressure dropped from a pre-operative pressure of 32 millimeters (Hg) to 10 millimeters (Hg) after the laser trabecular ablation procedure. Another subject's intraocular pressure dropped from about 28 millimeters (Hg) to 23 millimeters (Hg) after being treated with the 28 pulses of laser radiation at 50 millijoules per pulse applied over approximately two clock hours of the trabeculum.

In another experiment, twelve subjects with open angle glaucoma were treated. Each subject had uncontrolled intraocular pressure despite maximally tolerated medication. For each subject, up to 50 laser shots were applied to the trabecular meshwork. Energy per pulse was in the range of 30 to 80 millijoules. The spot size of the laser beam on the trabecular meshwork was in the range 100 to 200 microns.

One day after the procedure, the subjects showed a dramatic drop in intraocular pressure. Each subject showed a reduction in pressure of at least 10 millimeters (Hg). The average intraocular pressure reduction was in the range of 15 millimeters (Hg). some showed an intraocular pressure reduction of greater than 20 millimeters (Hg). After twelve months, about forty percent of the subjects' intraocular pressure was well controlled without any medication. Another twenty-five percent of the subjects have well controlled intraocular pressure with one medication.

The procedure has been shown to be equally effective in lowering intraocular pressure in subjects subjected to previous laser trabeculoplasty treatments and having continued uncontrolled intraocular pressure. In addition, there have been no significant complications, such as intraocular pressure spiking, observed with this procedure.

In a third experiment, a series of procedures were performed using autopsied human eyes. Laser pulses were applied to the trabecular meshwork using the procedure referred to above. A range of energies from 20 to 100 millijoules was used. The laser impact sites were then examined under electron microscopy. It was observed that at lower energies, no holes were created, but the trabecular meshwork had a "more open" appearance. At higher energies, holes in the meshwork extending into Schiemm's canal were observed.

An explanation for the pressure reduction effect of the present method is that the laser beam has been optimized to thermally ablate material disposed between the meshwork fibers without necessarily creating frank holes in the meshwork. As a result, the meshwork becomes "more open," thereby increasing the outflow facility. The tissue ablation achieved with minimal collateral thermal and mechanical damge in the present method is less likely to elicit an aggressive healing response so that long term pressure reduction can be achieved.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

We claim:

1. A non-invasive method of treating glaucoma in a human eye, the method comprising the steps of:

delivering a beam of pulsed laser radiation of wavelength betwveen 350 and 1300 nanometers, energy of 10 to 500 millijoules per pulse, pulse duration of 0.1 to 50 microseconds and spot size of up to 300 microns in diameter to a region of trabecular meshwork within a human eye;

thermally ablating the region with the beam of pulsed laser radiation to reduce intraocular pressure while minimizing damage to tissue surrounding the trabecular meshwork.

2. The method of claim 1 further comprising delivering the beam of pulsed laser radiation gonioscopically.

3. The method of claim 1 wherein the delivering step further comprises delivering a beam of pulsed laser radiation having a pulse duration of 1 to 50 microseconds.

4. The method of claim 1 wherein the delivering step further comprises delivering a beam of pulsed laser radiation having a wavelength between 700 and 900 nanometers.

5. The method of claim 1 wherein the delivering step further comprises delivering a beam of pulsed laser radiation having a per pulse energy of 25 to 250 millijoules.

6. The method of claim 1 wherein the delivering step further comprises delivering a beam of pulsed beam of laser radiation having a spot size of 50 to 300 microns in diameter.

7. A non-invasive method of treating glaucoma in a human eye, the method comprising the steps of:

generating a beam of pulsed laser radiation of wavelength between 350 and 1300 nanometers, energy of 10 to 500 millijoules per pulse, pulse duration of 0.1 to 50 microseconds, and spot_size of up to 200 microns in diameter using a solid state laser;

delivering the beam of pulsed laser radiation to a region of trabecular meshwork within a human eye;

thermally ablating material disposed between meshwork fibers of the region with the beam of pulsed laser radiation to reduce intraocular pressure while minimizing damage to tissue surrounding the trabecular meshwork.

8. A non-invasive method of treating open angle glaucoma in a human eye, the method comprising the steps of:

generating a beam of pulsed laser radiation of wavelength between 700 and 900 nanometers, energy of 25 to 500 millijoules per pulse, spot_size of 50 to 300 microns in diameter and pulse duration of 1 to 50 microseconds using a Ti:Sapphire laser;

delivering the beam of pulsed laser radiation gonioscopically to a targeted region of trabecular meshwork within a human eye; and thermally ablating the targeted region with the beam of pulsed laser radiation while minimizing damage to tissue surrounding the trabecular meshwork.

9. The method of claim 8 wherein the generating step further comprises generating a beam of pulsed laser radiation having a spotsize of 100 to 200 microns in diameter.

10. The method of claim 8 further comprising thermally ablating material disposed between meshwork fibers within the targeted region with the beam of pulsed laser radiation.

* * * * *

UNITED STATES PATENT AND TRADEMARK OFFICE
CERTIFICATE OF CORRECTION

PATENT NO. : 6,059,772
DATED : May 9, 2000
INVENTOR(S) : Hsia *et al.*

It is certified that error appears in the above-identified patent and that said Letters Patent is hereby corrected as shown below:

In Claim 1, column 7, line 20, delete the word "betwveen" and replace with --between--.

In Claim 7, column 8, line 9, delete the phrase "spot_size" and replace with --spot size--.

In Claim 8, column 8, line 22, delete the phrase "spot_size" and replace with --spot size--.

Signed and Sealed this

Twenty-second Day of May, 2001

*Attest:*

NICHOLAS P. GODICI

*Attesting Officer*    *Acting Director of the United States Patent and Trademark Office*